United States Patent
Wu et al.

(10) Patent No.: US 7,379,527 B2
(45) Date of Patent: May 27, 2008

(54) METHODS AND APPARATUS FOR CT CALIBRATION

(75) Inventors: Xiaoye Wu, Rexford, NY (US); Paavana Sainath, Oconomowoc, WI (US); Ferry Tamtoro, Oconomowoc, WI (US); Jean-Baptiste Thibault, Milwaukee, WI (US); Roy-Arnulf Helge Nilsen, Menomonee Falls, WI (US)

(73) Assignee: General Electric Company, Schenectady, NY (US)

( * ) Notice: Subject to any disclaimer, the term of this patent is extended or adjusted under 35 U.S.C. 154(b) by 3 days.

(21) Appl. No.: 11/315,938

(22) Filed: Dec. 22, 2005

(65) Prior Publication Data
US 2007/0147580 A1 Jun. 28, 2007

(51) Int. Cl.
*G01N 23/00* (2006.01)
(52) U.S. Cl. .............. 378/18; 378/207; 378/901
(58) Field of Classification Search ........... 378/4–20, 378/18, 98.11, 98.12, 156, 207, 210, 901
See application file for complete search history.

(56) References Cited

U.S. PATENT DOCUMENTS

| | | | |
|---|---|---|---|
| 4,789,930 A * | 12/1988 | Sones et al. | 378/207 |
| 5,734,691 A | 3/1998 | Hu et al. | 378/4 |
| 5,774,519 A * | 6/1998 | Lindstrom et al. | 378/18 |
| 5,845,003 A | 12/1998 | Hu et al. | 382/131 |
| 6,115,487 A * | 9/2000 | Toth et al. | 382/131 |
| 6,173,029 B1 | 1/2001 | Xie et al. | 378/4 |
| 6,651,018 B2 * | 11/2003 | Kropfeld et al. | 702/85 |
| 6,748,098 B1 | 6/2004 | Rosenfeld | 382/131 |
| 6,856,666 B2 * | 2/2005 | Lonn et al. | 378/8 |
| 6,987,833 B2 * | 1/2006 | Du et al. | 378/98.9 |
| 6,990,222 B2 * | 1/2006 | Arnold | 382/131 |
| 2002/0048347 A1 * | 4/2002 | Saito | 378/207 |
| 2004/0252811 A1 * | 12/2004 | Morita et al. | 378/207 |
| 2004/0264628 A1 * | 12/2004 | Besson | 378/5 |
| 2005/0084069 A1 * | 4/2005 | Du et al. | 378/98.9 |

OTHER PUBLICATIONS

US 6,055,290, 04/2000, Xie et al. (withdrawn)

* cited by examiner

*Primary Examiner*—Allen C. Ho
*Assistant Examiner*—Alexander Taningco
(74) *Attorney, Agent, or Firm*—Armstrong Teasdale LLP

(57) ABSTRACT

A method for normalizing a calibration of a computed tomographic (CT) imaging apparatus having a plurality of detector rows includes utilizing a prestored, predetermined inversion matrix and CT numbers obtained from images of a phantom to determine normalized calibration vectors for each row of a plurality of detector rows, and storing the determined normalized calibration vectors for each row of the plurality of detector rows in a memory for use in subsequent image reconstructions.

20 Claims, 3 Drawing Sheets

METHODS AND APPARATUS FOR CT CALIBRATION

BACKGROUND OF THE INVENTION

This invention relates generally to methods and apparatus for computed tomographic (CT) imaging, and more particularly to methods and apparatus for accurately calibrating CT imaging apparatus.

In some known CT imaging system configurations, an x-ray source projects a fan-shaped beam which is collimated to lie within an X-Y plane of a Cartesian coordinate system and generally referred to as an "imaging plane". The x-ray beam passes through an object being imaged, such as a patient. The beam, after being attenuated by the object, impinges upon an array of radiation detectors. The intensity of the attenuated radiation beam received at the detector array is dependent upon the attenuation of an x-ray beam by the object. Each detector element of the array produces a separate electrical signal that is a measurement of the beam intensity at the detector location. The intensity measurements from all the detectors are acquired separately to produce a transmission profile.

In third generation CT systems, the x-ray source and the detector array are rotated with a gantry within the imaging plane and around the object to be imaged such that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector.

In an axial scan, the projection data is processed to construct an image that corresponds to a two-dimensional slice taken through the object. One method for reconstructing an image from a set of projection data is referred to in the art as the filtered backprojection technique. This process converts the attenuation measurements from a scan into integers called "CT numbers" or "Hounsfield units" (HU), which are used to control the brightness of a corresponding pixel on a cathode ray tube display.

To reduce the total scan time, a "helical" scan may be performed. To perform a "helical" scan, the patient is moved while the data for the prescribed number of slices is acquired. Such a system generates a single helix from a fan beam helical scan. The helix mapped out by the fan beam yields projection data from which images in each prescribed slice may be reconstructed.

Reconstruction algorithms for helical scanning typically use helical weighing algorithms that weight the collected data as a function of view angle and detector channel index. Specifically, prior to a filtered backprojection process, the data is weighted according to a helical weighing factor, which is a function of both the gantry angle and detector angle. The weighted data is then processed to generate CT numbers and to construct an image that corresponds to a two-dimensional slice taken through the object.

To further reduce the total acquisition time, multi-slice CT has been introduced. In multi-slice CT, multiple rows of projection data are acquired simultaneously at any time instant. When combined with helical scan mode, the system generates a single helix of cone beam projection data. Similar to the single slice helical, weighting scheme, a method can be derived to multiply the weight with the projection data prior to the filtered backprojection algorithm.

In at least one known computed tomographic (CT) imaging system with fan beam reconstruction, CT number calibration is achieved using a simple algorithm that includes measuring each image of a phantom generated from 2D reconstruction, wherein each detector row contributes to one and only one image, and then adjusting a calibration vector. The calibration vector modification shifts the CT number by a constant value (including an air compensation), regardless of the size of the phantom.

However, in some cone-beam multi-slice CT systems, 3D image reconstruction is used, and any given image may contain contributions from a plurality of adjacent detector rows. Thus, simple measurement and scaling techniques based upon individual images may not provide satisfactory results.

BRIEF DESCRIPTION OF THE INVENTION

In one aspect, some configurations of the present invention provide a method for normalizing a calibration of a computed tomographic (CT) imaging apparatus having a plurality of detector rows. The method includes utilizing a prestored, predetermined inversion matrix and CT numbers obtained from images of a phantom to determine normalized calibration vectors for each row of a plurality of detector rows, and storing the determined normalized calibration vectors for each row of the plurality of detector rows in a memory for use in subsequent image reconstructions.

In another aspect, some configurations of the present invention provide a computed tomographic (CT) imaging apparatus having a plurality of detector rows and memory containing a prestored, predetermined inversion matrix. The apparatus is configured to utilize the prestored, predetermined inversion matrix and CT numbers obtained from images of a phantom to determine normalized calibration vectors for each row of a plurality of detector rows, and store the determined normalized calibration vectors for each row of the plurality of detector rows in a memory for use in subsequent image reconstructions.

In yet another aspect, some configurations of the present invention provide a medium or media having recorded thereon machine-readable instructions configured to instruct a processor to normalize a calibration of a computed tomographic (CT) imaging apparatus having a plurality of detector rows. The instructions include instructions to utilize a prestored, predetermined inversion matrix and CT numbers obtained from images of a phantom to determine normalized calibration vectors for each row of a plurality of detector rows, and instructions to store the determined normalized calibration vectors for each row of the plurality of detector rows in a memory for use in subsequent image reconstructions.

It will be appreciated that some configurations of the present invention provide improved capturing of individual contributions of each detector row to a 3D reconstructed image, and that some configurations of the present invention accurately normalize the HU numbers on CT images. Results from testing some configurations indicate that a single iteration of CT number adjustment is adequate in most cases.

DETAILED DESCRIPTION OF THE INVENTION

As used herein, an element or step recited in the singular and proceeded with the word "a" or "an" should be understood as not excluding plural said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property. For example, CT imaging apparatus embodiments may be described herein as having a plurality of detector rows that are used in a certain process. Such embodiments are not restricted from having other detector rows that are not used in that process.

Also as used herein, the phrase "reconstructing an image" is not intended to exclude embodiments of the present invention in which data representing an image is generated but a viewable image is not. However, many embodiments generate (or are configured to generate) at least one viewable image.

Figure 1:
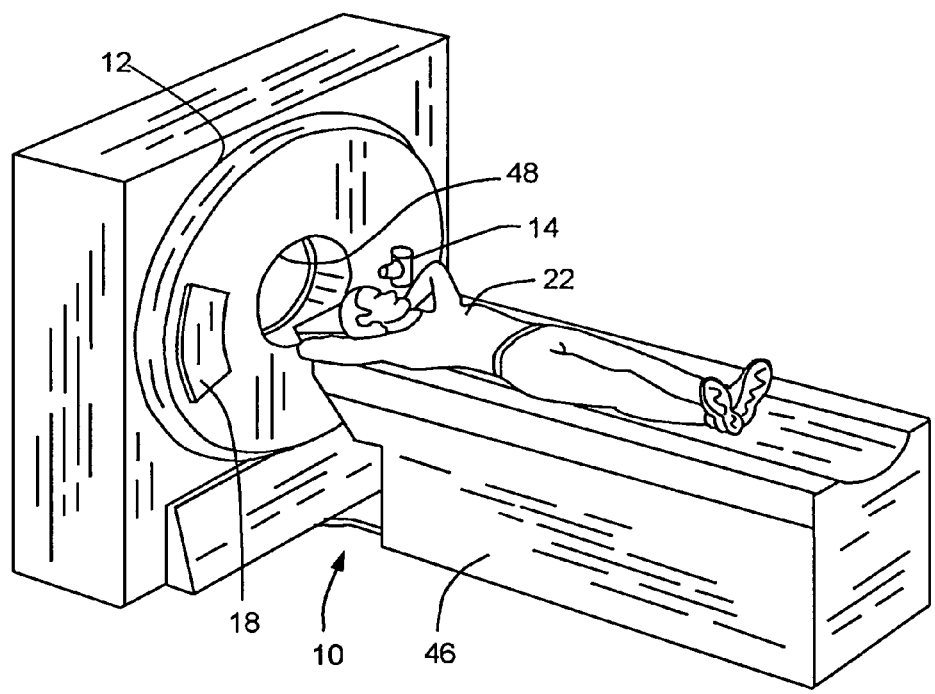
FIG. 1 is a pictorial diagram representative of some configurations of CT imaging systems of the present invention.
Figure 2:
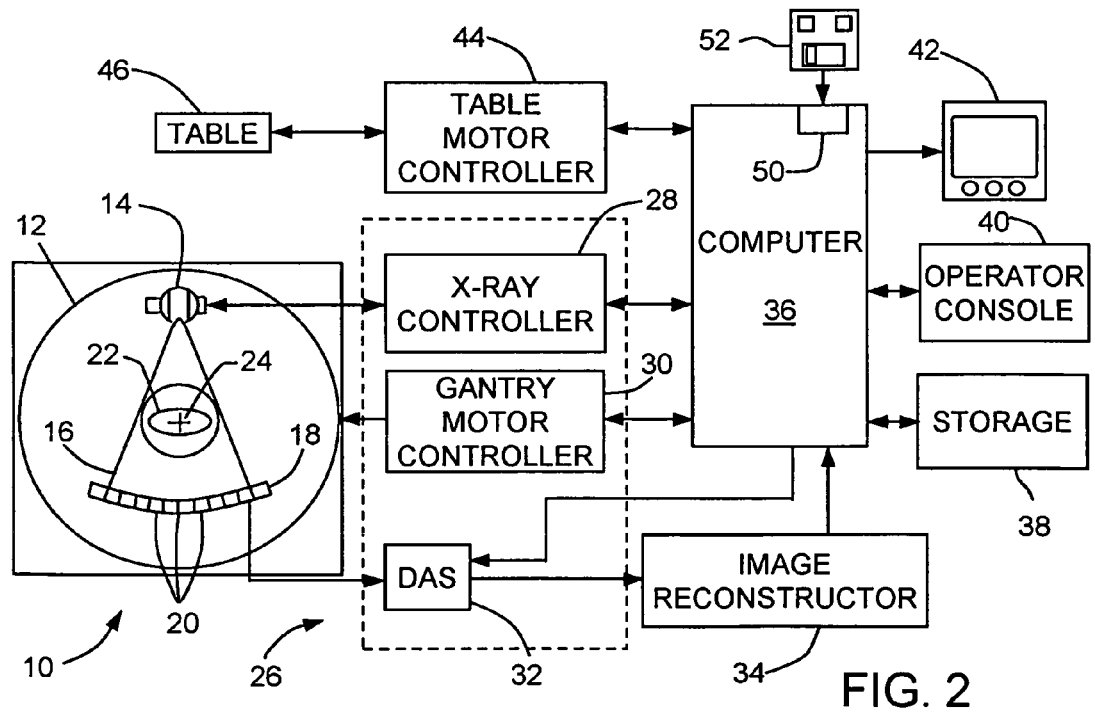
FIG. 2 is a functional block diagram of the CT imaging system of FIG. 1.

Referring to FIGS. 1 and 2, a multi-slice scanning imaging system, for example, a Computed Tomography (CT) imaging system 10, is shown as including a gantry 12 representative of a "third generation" CT imaging system. Gantry 12 has an x-ray tube 14 (also called x-ray source 14 herein) that projects a beam of x-rays 16 toward a detector array 18 on the opposite side of gantry 12. Detector array 18 is formed by a plurality of detector rows (not shown) including a plurality of detector elements 20 which together sense the projected x-rays that pass through an object, such as a medical patient 22 between array 18 and source 14. Each detector element 20 produces an electrical signal that represents the intensity of an impinging x-ray beam and hence can be used to estimate the attenuation of the beam as it passes through object or patient 22. During a scan to acquire x-ray projection data, gantry 12 and the components mounted therein rotate about a center of rotation 24. FIG. 2 shows only a single row of detector elements 20 (i.e., a detector row). However, multi-slice detector array 18 includes a plurality of parallel detector rows of detector elements 20 such that projection data corresponding to a plurality of quasi-parallel or parallel slices can be acquired simultaneously during a scan.

Rotation of components on gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of components on gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high-speed image reconstruction. The reconstructed image is applied as an input to a computer 36, which stores the image in a storage device 38. Image reconstructor 34 can be specialized hardware or computer programs executing on computer 36.

Computer 36 also receives commands and scanning parameters from an operator via console 40 that has a keyboard. An associated cathode ray tube (CRT), liquid crystal (LCD), plasma, or another suitable display device 42 allows the operator to observe the reconstructed image and other data from computer 36. The operator supplied commands and parameters are used by computer 36 to provide control signals and information to DAS 32, x-ray controller 28, and gantry motor controller 30. In addition, computer 36 operates a table motor controller 44, which controls a motorized table 46 to position patient 22 in gantry 12. Particularly, table 46 moves portions of patient 22 through gantry opening 48.

In one embodiment, computer 36 includes a device 50, for example, a floppy disk drive, CD-ROM drive, DVD drive, magnetic optical disk (MOD) device, or any other digital device including a network connecting device such as an Ethernet device for reading instructions and/or data from a computer-readable medium 52, such as a floppy disk, a CD-ROM, a DVD or another digital source such as a network or the Internet, as well as yet to be developed digital means. In another embodiment, computer 36 executes instructions stored in firmware (not shown). Computer 36 is programmed to perform functions described herein, and as used herein, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein.

It will be understood that the block diagram of FIG. 2 is closer to a logical representation of the functions described herein than a physical block diagram. Particular hardware and/or firmware and/or software implementations of these functions can be left as a design choice to one or more people skilled in the art of logic and/or computational circuit design and/or computer programming upon such person(s) gaining an understanding of the principles of the present invention presented herein.

Although the specific embodiment mentioned above refers to a third generation CT system, the methods described herein equally apply to fourth generation CT systems (stationary detector—rotating x-ray source) and fifth generation CT systems (stationary detector and x-ray source). Additionally, it is contemplated that the benefits of the invention accrue to imaging modalities other than CT. Additionally, although the herein described methods and apparatus are described in a medical setting, it is contemplated that the benefits of the invention accrue to non-medical imaging systems such as those systems typically employed in an industrial setting or a transportation setting, such as, for example, but not limited to, a baggage scanning system for an airport or other transportation center.

Figure 3:
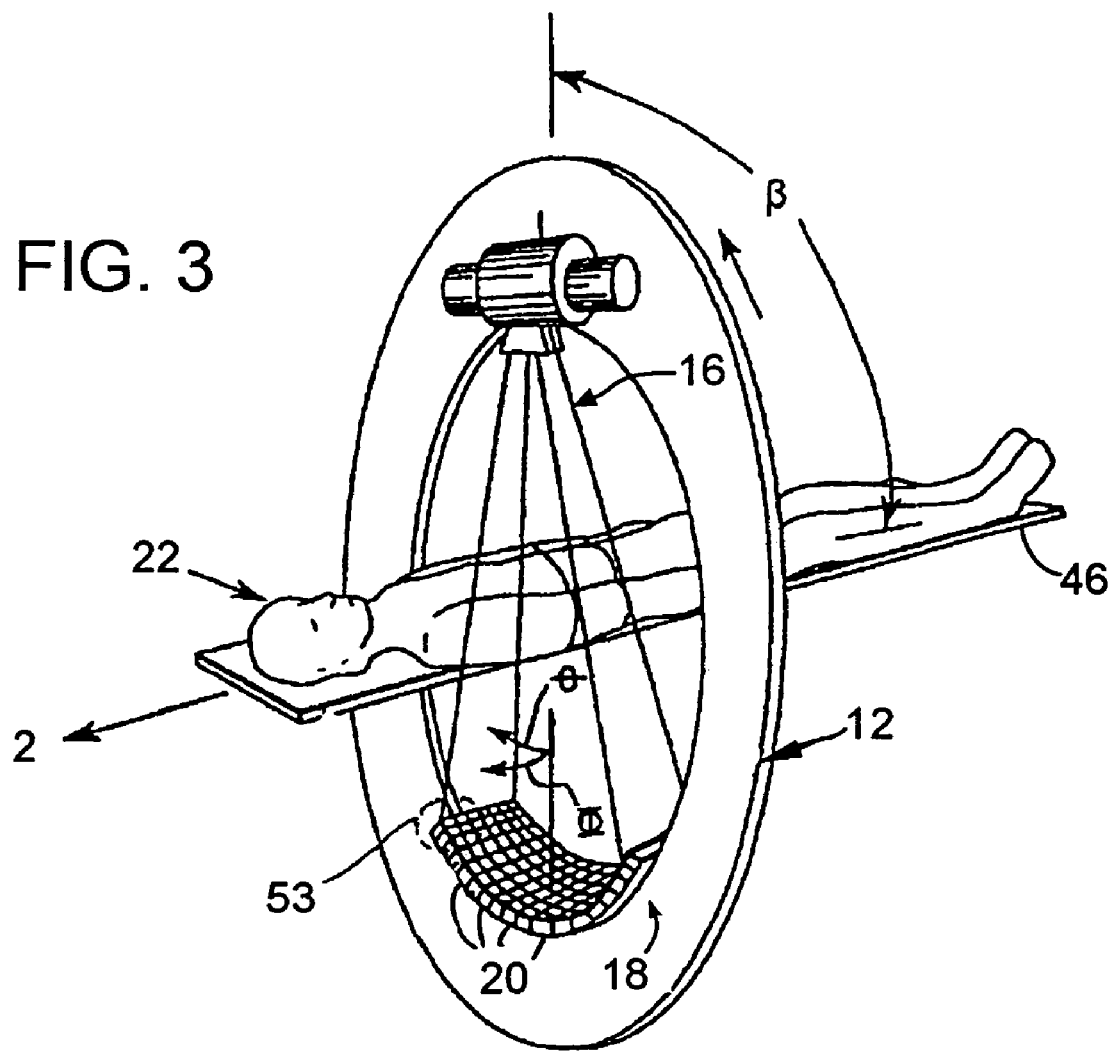
FIG. 3 is pictorial diagram showing some of the components of the CT imaging system of FIG. 1 and explicitly illustrating the multi-row detector array.

In some configurations and referring to FIG. 3, detector array 18 is a multirow detector array. Radiation source 14 and multirow ray detector array 18 are mounted on opposing sides of gantry 12 so that both rotate about an axis of rotation. The axis of rotation forms the z-axis of a Cartesian coordinate system having its origin centered within x-ray beam 16. The plane defined by the "x" and "y" axes of this coordinate system thus defines a plane of rotation, specifically the plane of gantry 12.

Rotation of gantry 12 is measured by an angle β from arbitrary reference position within plane of gantry 20. Angle β varies between 0 and 2π radians. X-ray beam 16 diverges from the gantry plane by an angle Φ and diverges along the gantry plane by angle Θ. Detector array 18 has a generally arcuate cross-sectional shape and its array of detector elements 20 are arranged to receive and make intensity measurements along the rays of x-ray beam 16 throughout the angles of Φ and Φ of radiation beam 16.

Detector array 18 comprises a 2-D array of detector elements 20 arranged in rows and columns. Each row comprises a plurality of detector elements 20 extending generally along an in-slice dimension. Each column comprises a plurality of detector elements extending generally parallel to the z-axis.

A technical effect of the present invention is the accurate calibration of calibration vectors in a CT imaging apparatus. This effect is achieved in some configurations by an operator operating the CT imaging apparatus (or another apparatus on which cone-beam projection data is used to generate images) having a plurality of detector rows includes utilizing a prestored, predetermined inversion matrix and CT numbers obtained from images of a phantom to determine normalized calibration vectors for each row of a plurality of detector rows, and storing the determined normalized calibration vectors for each row of the plurality of detector rows in a memory for use in subsequent image reconstructions. The determined calibration vectors for each row of the plurality of detector rows is stored in a memory for use in subsequent image reconstructions.

Figure 4:
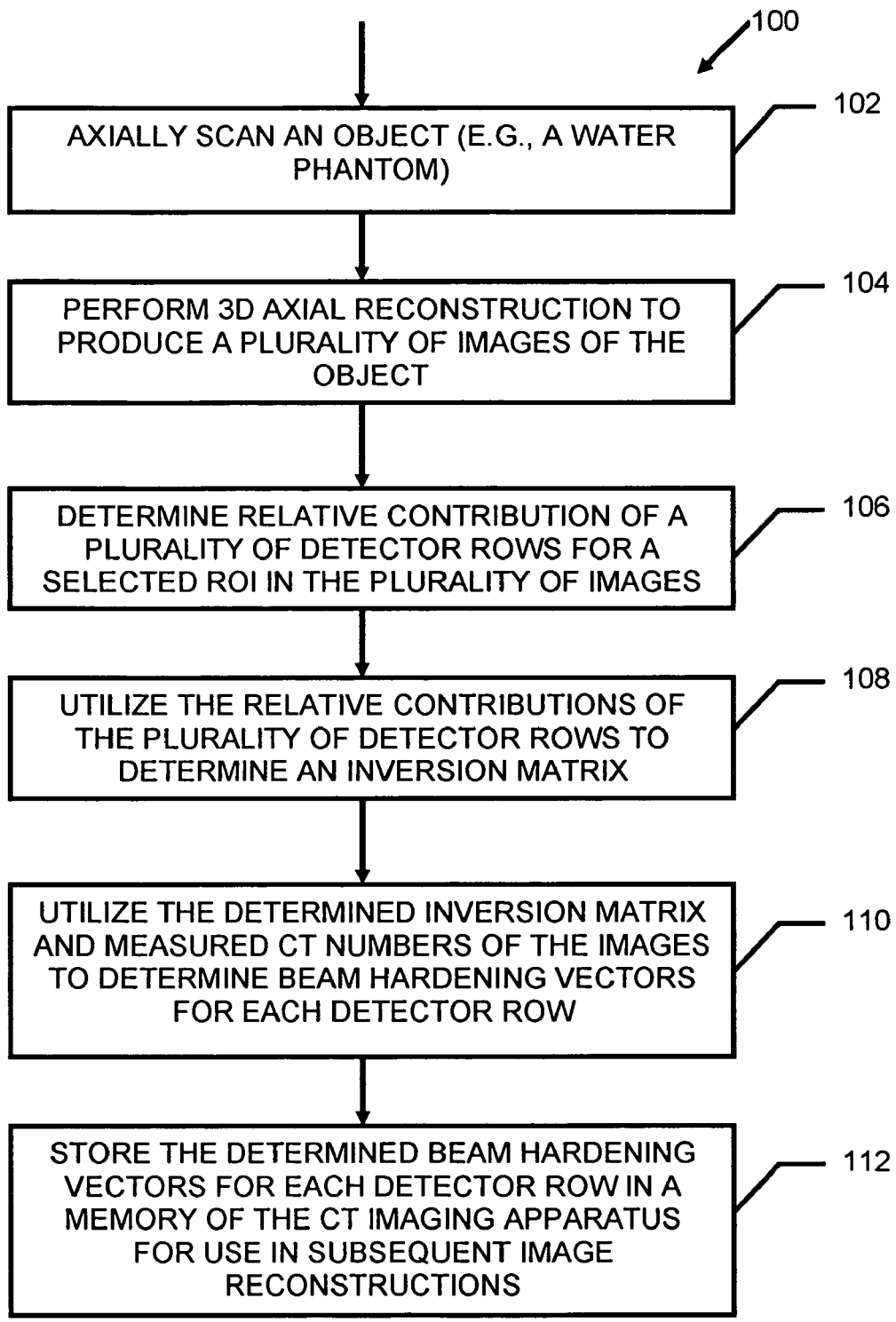
FIG. 4 is a flow chart representative of some calibration method configurations of the present invention.

More particularly and referring to flow chart 100 of FIG. 4, in some configurations of the present invention, CT imaging apparatus 10 is calibrated by operating CT imaging apparatus 10 to axially scan an object 22 (e.g., a phantom, or more particularly, a water phantom) at 102 to obtain projection data. A 3D axial reconstruction is performed at 104 to produce a plurality of images of object 22. Relative contributions of a plurality of rows of detector 18 for a selected region of interest (ROI), usually a circular area in the center of an image, are determined at 106. These relative contributions of the plurality of detector rows are used to predetermine an inversion matrix at 108. The predetermined inversion matrix is prestored in a memory of the CT apparatus, where it can then be used along with the measured CT numbers of the images to determine calibration vectors for each detector row at 110. (In this context, "prestored" and "predetermined" mean that the inversion matrix is determined and stored as a permanent calibration prior to actual use of the CT apparatus, as would generally be done by a manufacturer of the CT apparatus. In general, the same calibration matrix would be used for all CT apparatus of the same model.) The determined calibration vectors for each detector row are stored in a memory (e.g., a memory of computer 36) for use in subsequent image reconstuctions. Instructions configured to instruct a processor (such as a processor in computer 36) to perform the steps of the calibration process upon initiation of the process by an operator or technician may be stored in a memory of computer 36 and/or recorded on a computer readable medium such as medium 52. The selection of ROI may be pre-stored as data along with these instructions or instructions may be included to input an ROI via console 40. Configurations of the present invention are not limited to those in which computer 36, console 40, and medium 52 are used to perform calibration steps, but rather, the computational resources used for such calibration can be left as a design choice by one of ordinary skill in the art of computer design or digital circuit design. Moreover, a standalone computer or workstation (not shown) can be used for image reconstruction, and portions of the calibration process performed on this computer or workstation. Where such a computer or workstation is used, different calibration vectors can be stored for different CT imaging devices.

More particularly, to obtain a scaling factor for a CT number adjustment of a given row of detector array 18 (also referred to herein simply as detector 18 or multi-row detector 18), images produced in an axial scanning mode are used. In some configurations, all images are used, (for example all 64 images in a CT imaging apparatus 10 having a 64-row detector array 18). The calibration algorithm also involves scaling the spectral calibration vectors. The scaling method does not alter air value. Thus a more accurate CT number measurement is obtained in air regions.

Some configurations of the present invention this provide a CT number normalization method for 3D image reconstruction. Relative contributions of various detector rows to a selected ROI in a specific image generated from 3D axial reconstruction are obtained. In some configurations, these relative contributions are obtained using theoretical computations that depend upon the reconstruction algorithm used in a particular imaging system 10. In other configurations, they are be obtained by experimentation. One example of a suitable experimental procedure by which these relative contributions can be obtained includes obtaining fully-calibrated 20 cm water projection data with CT number values close to a target range (e.g., +/−6 HU). Next, images are reconstructed with the projection data thus obtained, and the CT numbers for all the images with a selected ROI at or near the center of the image are measured. The original polynomial beam hardening coefficient vectors of each detector row i are scaled by a scaling factor s=1.05, sequentially, and a new set of images are reconstructed. The CT numbers are then measured using the same ROI. The previously obtained CT numbers are then subtracted from the newly obtained CT numbers to obtain a difference matrix $x(i,j)$, where j is the image index. The matrix $x(i,j)$ is then normalized to a normalized matrix $m(i,j)$, where $m(i,j)=(1000.0+x(i,j))/1000.0$. The scaling step through the normalization step and all steps between are repeated for all detector rows i from 0 to 63, except that, in some configurations, row symmetry allows the repetition to be limited to only half of the rows, e.g., rows 0 to 31.

Using the measured data obtained above, configurations of the present invention also provide a process to obtain an inversion matrix. To obtain an inverted matrix $k(i,j)$ from the normalized weights of $m(i,j)$ obtained above, each $n(i,j)$ is set equal to $m(i,j)$ divided by the sum over index i of $m(i,j)$. Then, $k(i,j)$ is set equal to the inversion of $n(i,j)$, i.e., $k \times n=1$. In case a floating point underflow error is encountered in the inversion process, the following substitution is used:

if $(abs(k(i,j))$<threshold) then set $k(i,j)=0.0$.

A suitable value of the threshold in some configurations of the present invention is 0.0000001.

The computed inversion matrix k obtained in the above-described manner is independent of focal spot size and kVp settings. The inversion matrix depends only upon the reconstruction configuration used to reconstruct an axial image for HU normalization during the calibration process. In some configurations of the present invention, the computed $k(i,j)$ values are stored as part of a calibration data base.

Now, with knowledge of the inversion matrix, the scaling factor to normalize the calibration vectors is determined as follows. Let cal_vector (j) be a preexisting polynomial beam hardening coefficient vector for detector row j, needing water Hounsfield units normalizing. Let normalized_cal_vector (j) be a normalized cal vector for detector row j, and k (i, j) be the pre-determined inversion matrix. Then scaling (j)=scaling factor for detector row j to normalize its calibration vector Next, a scan a 20 cm water phantom is performed and an ROI is placed on the center of the phantom image. The mean intensity of the pixels in the water section of the phantom is then measured. Let this be h(i), where i is the image index. Then, H(i)=(1000.0+h(i))/1000.0 is the normalized measured mean intensity of water prior to normalization, $$\text{scaling}(j) = s(j) = \frac{1}{\sum_i (k(i, j) * H(i))}, \text{ and}$$

$$\text{normalized\_cal\_vector}(j) = \text{cal\_vector}(j) * \text{scaling}(j).$$

Thus, the individual contribution of each detector row to a 3D reconstructed image is captured, ensuring that the HU on each image is accurately normalized. Results from testing indicate that a single iteration of CT number adjustment is adequate in most cases.

Known methods used for setting CT numbers have been based on 2D reconstruction in which each axial image maps back onto exactly one row. However, configurations of the present invention provide advantageous results in cone beam multi-slice systems in which data from multiple rows are combined to form one image. More specifically, some configurations of the present invention achieve these results by generating row contributions and using weighting factors in a matrix operation to scale the calibration vectors so that CT numbers for each individual row are accurately set.

While the invention has been described in terms of various specific embodiments, those skilled in the art will recognize that the invention can be practiced with modification within the spirit and scope of the claims.

What is claimed is:

1. A method for normalizing a calibration of a computed tomographic (CT) imaging apparatus having a plurality of detector rows, said method comprising:
    utilizing a prestored, predetermined inversion matrix and CT numbers obtained from images of a phantom to determine normalized calibration vectors for each row of a plurality of detector rows, the normalized calibration vectors are based on a relative contribution of each of a plurality of projection data slices generated by the plurality of detector rows, the inversion matrix is determined from a difference matrix of CT numbers obtained from images reconstructed using the projection data and a scaled projection data of the same ROI;
    storing the determined normalized calibration vectors for each row of the plurality of detector rows in a memory for use in subsequent image reconstructions; and
    calibrating the CT imaging apparatus using the determined normalized calibration vectors.

2. A method in accordance with claim 1 wherein to obtain the CT numbers, said method comprises imaging a water phantom.

3. A method in accordance with claim 1 wherein said utilizing said CT numbers comprises averaging CT numbers in a region of interest (ROI) of the phantom.

4. A method in accordance with claim 3 further comprising determining a scaling factor for each detector row in accordance with the inversion matrix and the averaged CT numbers in the ROI.

5. A method in accordance with claim 1 wherein said images are 3D images.

6. A method in accordance with claim 1 further comprising generating an image of an object using the normalized calibration vectors.

7. A method in accordance with claim 6 wherein to obtain the CT numbers, said method comprises imaging a water phantom.

8. A method in accordance with claim 6 wherein said images are 3D images.

9. A computed tomographic (CT) imaging apparatus having a plurality of detector rows and memory containing a prestored, predetermined inversion matrix, and a computer configured to:
    utilize the prestored, predetermined inversion matrix and CT numbers obtained from images of a phantom to determine normalized calibration vectors for each row of a plurality of detector rows, the normalized calibration vectors are based on a relative contribution of each of a plurality of projection data slices generated by the plurality of detector rows, the inversion matrix is determined from a difference matrix of CT numbers obtained from images reconstructed using the projection data and a scaled projection data of the same RIO; and
    store the determined normalized calibration vectors for each row of the plurality of detector rows in a memory for use in subsequent image reconstructions.

10. An apparatus in accordance with claim 9 wherein further configured to average CT numbers in a region of interest (ROI) of the phantom.

11. An apparatus in accordance with claim 10 further configured to determine a scaling factor for each detector row in accordance with the inversion matrix and the averaged CT numbers in the ROI.

12. An apparatus in accordance with claim 9 wherein said images are 3D images.

13. An apparatus in accordance with claim 9 further configured to generate an image of an object using the normalized calibration vectors.

14. A computer program embodied on a computer readable medium, said computer program including at least one code segment configured to instruct a processor to normalize a calibration of a computed tomographic (CT) imaging apparatus having a plurality of detector rows by:
    utilizing a prestored, predetermined inversion matrix and CT numbers obtained from images of a phantom to determine normalized calibration vectors for each row of a plurality of detector rows, the normalized calibration vectors are based on a relative contribution of each of a plurality of projection data slices generated by the plurality of detector rows, the inversion matrix is determined from a difference matrix of CT numbers obtained from images reconstructed using the projection data and a scaled projection data of the same ROI;
    storing the determined normalized calibration vectors for each row of the plurality of detector rows in a memory for use in subsequent image reconstructions; and
    calibrating the CT imaging apparatus using the determined normalized calibration vectors.

15. A computer program in accordance with claim 14 further comprising a code segment configured to instruct the processor to obtain the CT numbers by imaging a water phantom.

16. A computer program in accordance with claim 14 further comprising a code segment configured to instruct the processor to utilize said CT numbers by averaging CT numbers in a region of interest (ROI) of the phantom.

17. A computer program in accordance with claim 16 further comprising a code segment configured to instruct the processor to determine a scaling factor for each detector row in accordance with the inversion matrix and the averaged CT numbers in the ROI.

18. A computer program in accordance with claim 14 wherein said images are 3D images.

19. A computer program in accordance with claim 14 further comprising a code segment configured to instruct the processor to generate an image of an object using the normalized calibration vectors.

20. A computer program in accordance with claim 19 further comprising a code segment configured to instruct the processor to obtain the CT numbers by imaging a water phantom with 3D images.

* * * * *